United States Patent [19]

Alessandrini et al.

[11] Patent Number: 6,150,401

[45] Date of Patent: *Nov. 21, 2000

[54] USE OF MEK1 INHIBITORS AS PROTECTIVE AGENTS AGAINST DAMAGE DUE TO ISCHEMIA

[75] Inventors: Alessandro Alessandrini, Cambridge; Joseph Bonventre, Wayland; Michael A. Moskowitz, Belmont, all of Mass.; Shobu Namura, Osaka, Japan

[73] Assignee: The General Hospital Corporation, Boston, Mass.

[*] Notice: This patent issued on a continued prosecution application filed under 37 CFR 1.53(d), and is subject to the twenty year patent term provisions of 35 U.S.C. 154(a)(2).

[21] Appl. No.: 09/226,080

[22] Filed: Jan. 6, 1999

Related U.S. Application Data

[60] Provisional application No. 60/070,530, Jan. 6, 1998.

[51] Int. Cl.[7] .................................................. A61K 31/35
[52] U.S. Cl. ............................................................ 514/456
[58] Field of Search ............................................. 514/456

[56] References Cited

U.S. PATENT DOCUMENTS

| | | | |
|---|---|---|---|
| 5,459,144 | 10/1995 | Girijavallabhan et al. | |
| 5,525,625 | 6/1996 | Bridges et al. | 514/456 |
| 5,633,237 | 5/1997 | Hansen, Jr. et al. | |
| 5,717,100 | 2/1998 | Selnick et al. | 546/194 |
| 5,849,733 | 12/1998 | Kim | 514/212 |

OTHER PUBLICATIONS

Bederson et al., Stroke 17:1304–1308, 1986.
Uemura et al., Brain Res. 542:343–347, 1991.
Hu et al., J. Neurochemistry 62:1357–1367, 1994.
Huang et al., Science 265:1883–1885, 1994.
Seko et al., Circ. Res. 78:82–90, 1996.
Aikawa et al., J. Biol. Chem. 100:1813–1821, 1997.
Muller et al., J. Biol. Chem. 272:23435–23439, 1997.
Kindy, J. Cer. Blood Flow and Metab. 13:372–377, 1993.
Namura et al., Stroke 29:326(P142), Jan. 1998.
Mizukami et al., Biochem. J. 323:785–790, 1997.
Dufourney et al., J. of Biol. Chem. 272(49):31163–31171, Dec. 5, 1997.

*Primary Examiner*—Raymond Henley, III
*Attorney, Agent, or Firm*—Wolf, Greenfield & Sacks, P.C.

[57] ABSTRACT

The invention relates to the use of MEK1 inhibitors to reduce tissue damage resulting from ischemia and/or reperfusion, particularly brain damage associated with ischemia resulting from stroke. Pharmaceutical compositions, kits and perfusion fluids including MEK1 inhibitors are also provided.

11 Claims, 5 Drawing Sheets

REDUCTION IN ERK1/2 PHOSPHORYLATION
IN THE PRESENCE OF PD98059

DMSO     PD98059

USE OF MEK1 INHIBITORS AS PROTECTIVE AGENTS AGAINST DAMAGE DUE TO ISCHEMIA

RELATED APPLICATIONS

This application claims priority under 35 U.S.C. §119 from U.S. provisional application Serial No. 60/070,530, filed Jan. 6, 1998.

GOVERNMENT SUPPORT

This work was funded in part by the National Institutes of Health under grant number 5P50NS10828-21. The government may retain certain rights in this invention.

FIELD OF THE INVENTION

The invention relates to treatments for tissue damage associated with ischemia, particularly brain damage associated with ischemia resulting from stroke.

BACKGROUND OF THE INVENTION

Ischemic diseases are significant causes of mortality in industrialized nations. It is well established that tissue damage results from ischemia (stoppage of blood flow to the tissue) followed by reperfusion of the tissue. The ischemic injury with the consecutive reperfusion is responsible for the disturbance of microcirculation with ensuing tissue damage and organ dysfunction.

One well-known example of ischemia and its effects is stroke, which is a condition resulting from a reduction or blockage of blood flow to the brain (cerebral ischemia). About 500,000 Americans suffer strokes each year, 80% of which are caused by a blood clot blocking one of the cerebral blood vessels. Symptoms of stroke include weakness, numbness or paralysis of the face, arm or leg; sudden loss or dimness of vision; loss of speech or difficulty using or understanding language; sudden, severe unexplained headache; or unexplained dizziness, unsteadiness or sudden falls (particularly if associated with one of the above symptoms).

Other organs are also affected by ischemia. For example, tissues such as kidney, heart, liver, pancreas, lung, intestine, are also known to sustain damage following ischemia and reperfusion.

The phosphorylation of ERK/MAP kinase in response to brain ischemia has been demonstrated previously. However, it is not known what, if any, role the ERK/MAP kinase pathway plays in the causation of tissue damage following ischemia and/or reperfusion.

SUMMARY OF THE INVENTION

It has now been discovered that MEK1 kinase activity is involved in ischemia-induced tissue damage. Using a mouse model of stroke in which focal cerebral ischemia is induced by middle cerebral artery occlusion, it has been demonstrated that a specific MEK1 inhibitor can decrease the tissue damage which results from ischemia and reperfusion.

According to one aspect of the invention, a method for treating a subject having a condition characterized by ischemia is provided. The method includes administering to a subject in need of such treatment a MEK1 inhibitor in an amount effective to reduce MEK1 activity, wherein the subject is free of symptoms otherwise calling for treatment with the MEK1 inhibitor. In certain embodiments, the symptoms otherwise calling for treatment with the MEK1 inhibitor are the symptoms of a proliferative disease. In other embodiments, the MEK1 inhibitor is selected from the group consisting of small molecule organic compounds, inhibitory antibodies, synthetic kinase substrate peptides, dominant negative MEK1 proteins, antisense nucleic acids, and ribozymes which reduce the expression of translatable MEK1 transcripts. Preferably the MEK1 inhibitor is a small molecule organic compound, particularly a tricyclic flavone. In particularly preferred embodiments, the MEK1 inhibitor is 2-(2-amino-3-methoxyphenyl)-4-oxo-4H-[1]benzopyran. In other preferred embodiments, the MEK1 inhibitor is administered to a subject who has had an ischemic stroke, or is administered prophylactically to a subject at risk of having an ischemic stroke.

According to another aspect of the invention, a pharmaceutical composition is provided. The pharmaceutical composition includes a MEK1 inhibitor and a non-MEK1 inhibitor anti-stroke agent, together in an amount effective for treating an ischemic condition. Preferred inhibitors and agents are as described elsewhere.

According to still another aspect of the invention, a kit is provided. The kit includes a package housing a first container containing a MEK1 inhibitor, and instructions for using the MEK1 inhibitor in the treatment of an ischemic condition. In certain embodiments, the kit also includes a second container containing a non-MEK1 inhibitor anti-stroke agent.

According to another aspect of the invention, a medical product is provided which includes an isolated organ in a perfusion fluid containing a MEK1 inhibitor.

According to another aspect of the invention, a medical product is provided which includes an organ perfusion fluid containing a MEK1 inhibitor.

In another aspect of the invention, the use of the foregoing MEK1 inhibitors in the preparation of a medicament for the foregoing treatments of conditions characterized by ischemia, particularly stroke, is provided.

These and other objects of the invention will be described in further detail in connection with the detailed description of the invention.

DETAILED DESCRIPTION OF THE INVENTION

Ischemia is a condition characterized by a stoppage of blood flow to a tissue or organ. The stoppage may result from a blockage in the blood vessel supplying the tissue or organ (e.g. a stroke), or may result when the heart stops beating (e.g. a heart attack). Reperfusion is the term which describes the restarting of the supply of blood to the organ or tissue following ischemia.

The present invention utilizes the unexpected finding that classes of compounds (MEK1 inhibitors) can relieve damage due to ischemia by inhibiting the MEK1 kinase. MEK1 is a dual specificity kinase that activates the MAP kinases ERK1 and ERK2 by phosphorylation on threonine and tyrosine. A MEK1 inhibitor, as used herein, is a compound which inhibits MEK1 kinase activity. By inhibition of MEK1 activity is meant the partial or complete inhibition of the MEK1 kinase activity in the affected tissue. This may be a reduction in the kinase activity of MEK1 to a level below that found under normal physiological conditions (which may vary from subject to subject) if used prophylactically or below that found under the conditions prevailing in the ischemic tissue if used acutely.

Compounds which are useful as MEK1 inhibitors include compounds which act on the MEK1 protein to directly inhibit MEK1 activity and compounds which indirectly inhibit MEK1 activity by reducing MEK1 expression at the stages of transcription and/or translation of the MEK1 gene. Inhibitors of MEK1 activity include compounds which bind to MEK1 and inhibit the enzymatic activity, including small molecule organic compounds, inhibitory antibodies, synthetic kinase substrate peptides and the like. Inhibitors of MEK1 activity also include variants of MEK1 having reduced activity, e.g. dominant negative MEK1 proteins having an inactivated kinase. Compounds which reduce MEK1 expression include antisense nucleic acids and ribozymes which reduce the expression of translatable MEK1 transcripts.

Preferred MEK1 inhibitors are flavone compounds and particularly preferred is the flavone compound 2-(2-amino-3-methoxyphenyl)-4-oxo-4H-[1]benzopyran (also known as 2'-amino-3'-methoxyflavone) described in U.S. Pat. No. 5,525,625. The formula of the compound is:

Variants of the foregoing flavone compound which retain the MEK1 inhibitory activity of the foregoing flavone compound also can be used in accordance with the invention. For example, different alkyl groups can be substituted for the methyl group at the 3 position of the phenyl ring. As one example, an ethyl group can be substituted for the methyl group to prepare the 3-ethoxy flavone derivative. Other examples of alkyl substitutions will be known to one of ordinary skill in the art and are not detailed further here. Still other types of chemical modifications can be made to the foregoing flavone to prepare compounds useful in the methods detailed herein, and such compounds tested for MEK1 inhibitory activity as detailed herein and in U.S. Pat. No. 5,525,625, with no more than routine experimentation.

As mentioned above, the invention embraces the use of antisense oligonucleotides that selectively bind to a nucleic acid molecule encoding a MEK1 polypeptide, to decrease MEK1 transcription or translation. Antisense molecules, in this manner, can be used to decrease or prevent the effects of ischemia mediated by MEK1.

As used herein, the term "antisense oligonucleotide" or "antisense" describes an oligonucleotide that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and, thereby, inhibits the transcription of that gene and/or the translation of that mRNA. The antisense molecules are designed so as to interfere with transcription or translation of a target gene upon hybridization with the target gene or transcript. Those skilled in the art will recognize that the exact length of the antisense oligonucleotide and its degree of complementarity with its target will depend upon the specific target selected, including the sequence of the target and the particular bases which comprise that sequence. It is preferred that the antisense oligonucleotide be constructed and arranged so as to bind selectively with the target under physiological conditions, i.e., to hybridize substantially more to the target sequence than to any other sequence in the target cell under physiological conditions. Based upon the MEK1 cDNA sequence (GenBank accession numbers L02526 (mouse) and L1284 (human)), or upon allelic or homologous genomic and/or cDNA sequences, one of skill in the art can easily choose and synthesize any of a number of appropriate antisense molecules for use in accordance with the present invention. In order to be sufficiently selective and potent for inhibition, such antisense oligonucleotides should comprise at least 10 and, more preferably, at least 15 consecutive bases which are complementary to the target, although in certain cases modified oligonucleotides as short as 7 bases in length have been used successfully as antisense oligonucleotides (Wagner et al., *Nature Biotechnol.* 14:840–844, 1996). Most preferably, the antisense oligonucleotides comprise a complementary sequence of 20–30 bases. Although oligonucleotides may be chosen which are antisense to any region of the gene or mRNA transcripts, in preferred embodiments the antisense oligonucleotides correspond to N-terminal or 5' upstream sites such as translation initiation, transcription initiation or promoter sites. In addition, 3'-untranslated regions may be targeted. Targeting to mRNA splicing sites has also been used in the art but may be less preferred if alternative mRNA splicing occurs. In addition, the antisense is targeted, preferably, to sites in which mRNA secondary structure is not expected (see, e.g., Sainio et al., *Cell Mol. Neurobiol.* 14(5):439–457, 1994) and at which proteins are not expected to bind. Finally, one of ordinary skill in the art may easily derive the genomic DNAs corresponding to the MEK1 cDNAs and thus the present invention also provides for the use of antisense oligonucleotides which are complementary to MEK1 genomic DNAs. Similarly, the use of antisense to MEK1 cDNAs and genomic DNAs of other species are enabled without undue experimentation.

In one set of embodiments, the antisense oligonucleotides of the invention may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleotide linkage. These oligonucleotides may be prepared by art recognized methods which may be carried out manually or by an automated synthesizer. They also may be produced recombinantly by vectors.

In preferred embodiments, however, the antisense oligonucleotides of the invention also may include "modified" oligonucleotides. That is, the oligonucleotides may be modified in a number of ways which do not prevent them from hybridizing to their target but which enhance their stability or targeting or which otherwise enhance their therapeutic effectiveness.

The term "modified oligonucleotide" as used herein describes an oligonucleotide in which (1) at least two of its nucleotides are covalently linked via a synthetic internucleoside linkage (i.e., a linkage other than a phosphodiester linkage between the 5' end of one nucleotide and the 3' end of another nucleotide) and/or (2) a chemical group not normally associated with nucleic acids has been covalently attached to the oligonucleotide. Preferred synthetic internucleoside linkages are phosphorothioates, alkylphosphonates, phosphorodithioates, phosphate esters, alkylphosphonothioates, phosphoramidates, carbamates, carbonates, phosphate triesters, acetamidates, carboxymethyl esters and peptides.

The term "modified oligonucleotide" also encompasses oligonucleotides with a covalently modified base and/or sugar. For example, modified oligonucleotides include oligonucleotides having backbone sugars which are covalently attached to low molecular weight organic groups other than a hydroxyl group at the 3' position and other than a phosphate group at the 5' position. Thus modified oligonucleotides may include a 2'-O-alkylated ribose group. In addition, modified oligonucleotides may include sugars such as arabinose instead of ribose. The present invention, thus, contemplates the use of pharmaceutical preparations containing modified antisense molecules that are complementary to and hybridizable with, under physiological conditions, nucleic acids encoding MEK1 polypeptides, together with pharmaceutically acceptable carriers.

The invention also provides, in certain embodiments, the use of "dominant negative" MEK1 polypeptides. A dominant negative polypeptide is an inactive variant of a protein, which, by interacting with the cellular machinery, displaces an active protein from its interaction with the cellular machinery or competes with the active protein, thereby reducing the effect of the active protein. For example, dominant negative MEK1 proteins include MEK1 proteins having a catalytically-inactive kinase domain which interacts normally with target proteins but does not phosphorylate the target proteins, or which does not interact with normally with target proteins, or both. Dominant negative MEK1 proteins include variants in which a portion of the kinase domain has been mutated or deleted to reduce or eliminate substrate binding or kinase activity.

The end result of the expression of a dominant negative MEK1 polypeptide in a cell is a reduction in function of active proteins. One of ordinary skill in the art can assess the potential for a dominant negative variant of a protein, and using standard mutagenesis techniques to create one or more dominant negative variant polypeptides. For example, given the nucleotide sequence of MEK1, one of ordinary skill in the art can modify the sequence of the MEK1 polypeptide by site-specific mutagenesis, scanning mutagenesis, partial gene deletion or truncation, and the like. See, e.g., U.S. Pat. No. 5,580,723 and Sambrook et al., *Molecular Cloning: A Laboratory Manual*, Second Edition, Cold Spring Harbor Laboratory Press, 1989. The skilled artisan then can test the population of mutagenized polypeptides for diminution in a selected activity (e.g., MEK1 kinase activity). Other similar methods for creating and testing dominant negative variants of a protein will be apparent to one of ordinary skill in the art.

The invention also embraces MEK1 binding agents which can be antibodies or fragments of antibodies having the ability to selectively bind to MEK1 polypeptides. Such agents can be used to inhibit the native activity of the MEK1 polypeptides by binding to such polypeptides. Antibodies include polyclonal and monoclonal antibodies, prepared according to conventional methodology.

Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an $F(ab')_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. Thus, for example, PCT International Publication Number WO 92/04381 teaches the production and use of humanized murine RSV antibodies in which at least a portion of the murine FR regions have been replaced by FR regions of human origin. Such antibodies, including fragments of intact antibodies with antigen-binding ability, are often referred to as "chimeric" antibodies.

Thus, as will be apparent to one of ordinary skill in the art, the present invention also provides for $F(ab')_2$, Fab, Fv and Fd fragments; chimeric antibodies in which the Fc and/or FR and/or CDR1 and/or CDR2 and/or light chain CDR3 regions have been replaced by homologous human or non-human sequences; chimeric $F(ab')_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

Several tests can be used to identify compounds which are specific inhibitors of MEK1 activity. For example U.S. Pat. No. 5,525,625, the disclosure of which is incorporated herein by reference, describes several assays which are useful for determining the MEK1 inhibitory potential of a test compound. The assays include in vitro kinase assays, whole cell kinase assays, and cell growth assays including assays of monolayer growth and growth in soft agar. The Examples below provide an in vivo assay of focal cerebral ischemia for testing the activity of MEK1 inhibitors. If the test compound is able to inhibit the MEK1 activity, then it is a compound which is useful in the treatment of ischemia, particularly stroke. The test compound can be determined readily to be a specific inhibitor of MEK1 activity.

The present invention is useful whenever it is desirable to prevent, inhibit altogether or reduce damage due to ischemia. The invention thus is useful in the treatment of ischemia, particularly in the prophylactic treatment of ischemia. In particular, the methods of treatment disclosed herein can be used to reduce brain injury resulting from strokes and/or perioperative ischemia during neural surgery. The methods of treatment disclosed herein can be used to reduce tissue injury resulting from ischemia in other organs including heart, kidney, pancreas, lung, intestine and the like.

The invention is particularly directed to a patient population never before treated with drugs useful according to the methods of the invention, including patients who are not suffering from a proliferative disorder such as cancer, psoriasis or restenosis. In other words, the treatment preferably is directed to patient populations that otherwise are free of symptoms that call for treatment with any of the drugs useful according to the invention.

When administered, the formulations of the invention are applied in pharmaceutically acceptable amounts and in pharmaceutically acceptable compositions. Such preparations may routinely contain salts, buffering agents, preservatives, compatible carriers, and optionally other therapeutic ingredients. Such pharmacologically and pharmaceutically acceptable salts include, but are not limited to, those prepared from the following acids: hydrochloric, hydrobromic, sulphuric, nitric, phosphoric, maleic, acetic, salicylic, p-toluene sulfonic, tartaric, citric, methane sulfonic, formic, malonic, succinic, naphthalene-2-sulfonic, and benzene sulfonic. Also, pharmaceutically acceptable salts can be prepared as alkaline metal or alkaline earth salts, such as sodium, potassium or calcium salts of the carboxylic acid group.

The compounds useful in the invention may be delivered in a mixture with other anti-ischemia agents (particularly anti-stroke agents) which are non-MEK1 inhibitors. A non-MEK1 inhibitor anti-stroke agent is an anti-stroke agent which is not a MEK1 inhibitor as defined herein. One of ordinary skill in the art is familiar with a variety of non-MEK1 inhibitor anti-stroke agents which are used in the medical arts to treat ischemia such as stroke (e.g., thrombotic, embolic and/or hemorrhagic stroke). Such agents include antiplatelet agents, anticoagulation agents, thrombolytic agents including plasminogen activators, antithrombotics, neuroprotective agents, platelet activating factor antagonists, platelet aggregation inhibitors, post-stroke and post-head trauma treatments, cerebral ischemia agents, basic fibroblast growth factors and steroids Antiplatelet agents, which inhibit platelet aggregation, include aspirin, ticlopidine and dipyridamole.

Anticoagulation agents reduce or prevent the coagulation of blood components and thus reduce or prevent clot formation; common anticoagulation agents include coumarin and heparin.

Thrombolytic agents function by lysing the clot which causes the ischemia. Commonly used thrombolytic agents include urokinase, streptokinase and tissue plasminogen activator (alteplase, tPA). Various modified forms of tPA ("modified tPA") have been characterized and are known to those skilled in the art. Modified tPA includes, but is not limited to, variants having deleted or substituted amino acids or domains, variants conjugated to other molecules, and variants having modified glycosylation. For example, PCT Publication No. WO93/24635 discloses tPA variants having an extra glycosylation site at any of the amino acid positions 103–105 and the native glycosylation site removed at position 117 of the native human tPA. The amino acid number refers to the amino acid in that position of the mature, wild-type tPA polypeptide as disclosed in U.S. Pat. No. 4,766,075. The disclosed variants may also include at least one amino acid substituted in the 296–299 position with alanine and/or a substitution of the amino acids at positions 274–277 of wild type tPA (phenylalanine, arginine, isoleucine, lysine) with leucine, histidine, serine, and threonine, respectively. Triple mutants of tPA also are disclosed, including the specific molecule: T103N, N117Q, KHRR (296–299) AAAA t-PA (TNK t-PA). EP 352,119 discloses vampire bat tPAs (Bat-PAs (H), (I), and (L)). Vampire bat-PAs are variants of native tPA having a variety of sequence modifications. Suzuki et al., (*J. Cardiovasc. Pharmacal.* 22:834–840, 1993) disclose tPA variants in which a cysteine at position 84 of the growth factor domain of native tPA is replaced by serine (C84S tPA). Although this variant retains the functional activity of native tPA, it has been shown to have a longer in vivo half life than native tPA.

Variants of tPA have been developed which retain tPA functionality but have reduced clearance rates. These variants include tPA molecules with deleted amino acids or domains, such as those described by Johannessen et al. (*Throm. Haemostas.* 63:54–59, 1990) and Sobel et al. (*Circulation* 81:1362–73, 1990); tPA molecules which have amino acid substitutions in the regions of 63–72 and 42–49, such as those described by Ahem et al. (*J. Biol. Chem.* 265:5540, 1990); and tPA molecules which have a glutamic acid substituted for the arginine at position 275 of the native t-PA molecule such as that described by Hotchkiss et al. (*Throm. Haemostas.* 55:491, 1987). tPA molecules conjugated to other molecules have also been found to have decreased clearance rates. For example, conjugation of tPA to polyethylene glycol has been shown to reduce the clearance rate of tPA, as disclosed in EP-A304,311. Conjugation of a tPA molecule to a monoclonal antibody has been shown to increase the half-life of tPA in vivo (EP A339,505).

Modification of glycosylation on native tPA has also been found to have an effect on clearance rates of tPA. PCT application WO89/11531 discloses several tPA variants having additional glycosylation sites, which also have decreased clearance rates. Other research has described tPA variants with reduced glycosylation, which also exhibit decreased clearance rates (Martin et al., *Fibrinolysis* 4:9, 1990). Each of the above references is hereby incorporated by reference.

Antithrombotics include anagrelide hydrochloride; bivalirudin ; dalteparin sodium; danaparoid sodium; dazoxiben hydrochloride; efegatran sulfate; enoxaparin sodium; ifetroban; ifetroban sodium; tinzaparin sodium ; and trifenagrel.

Neuroprotective agents include dizocilpine maleate.

Cardioprotectant agents including MPL-C, adenosine, and acadesine.

Platelet activating factor antagonists include lexipafant.

Platelet aggregation inhibitors include acadesine; beraprost; beraprost sodium; ciprostene calcium; itazigrel; lifarizine; oxagrelate.

Post-stroke and post-head trauma agents include citicoline sodium (cytidine 5'-diphosphocholine).

Cerebral ischemia agents include dextrorphan hydrochloride.

The formulations of the invention are administered in effective amounts, alone or in a cocktail with one or more of the foregoing compounds. An effective amount is one sufficient to inhibit MEK1 activity, thereby effectively decreasing or preventing the deleterious effects of ischemia. Effective amounts will depend, of course, on the severity of the condition being treated; individual patient parameters including age, physical condition, size and weight; concurrent treatment; frequency of treatment; and the mode of administration. These factors are well known to those of ordinary skill in the art and can be addressed with no more than routine experimentation. It is preferred generally that a maximum dose be used, that is, the highest safe dose according to sound medical judgment.

Dosages are estimated based on the inhibition of MEK1 activity and the inhibition of the effects of ischemia in experimental models. Generally, daily oral prophylactic doses of active compounds will be from about 0.01 milligrams/kg per day to 2000 milligrams/kg per day. It is expected that oral doses in the range of 10 to 500 milligrams/kg, in one or several administrations per day, will yield the desired results. In the event that the response in a subject is insufficient at such doses, even higher doses (or effective higher doses by a different, more localized delivery route) may be employed to the extent that patient tolerance permits. Dose ranges can be adjusted as necessary for the treatment of ischemia in organs other than brain, i.e., other than for the treatment of stroke. Multiple doses per day are contemplated to achieve appropriate systemic levels of compounds.

A variety of administration routes are available. The particular mode selected will depend of course, upon the particular drug selected, the severity of the migraine state being treated and the dosage required for therapeutic efficacy. The methods of this invention, generally speaking, may be practiced using any mode of administration that is medically acceptable, meaning any mode that produces effective levels of the active compounds without causing clinically unacceptable adverse effects. Such modes of administration include oral, rectal, topical, nasal, transdermal or parenteral routes. The term "parenteral" includes subcutaneous, intravenous, intramuscular, or infusion. Intravenous and intramuscular routes are not particularly suited for long term therapy and prophylaxis. They could, however, be preferred in acute emergency situations. Oral administration will be preferred for prophylactic treatment because of the convenience to the patient as well as the dosing schedule.

The compositions may conveniently be presented in unit dosage form and may be prepared by any of the methods well known in the art of pharmacy. In general, the compositions are prepared by uniformly and intimately bringing the active compounds into association with a liquid carrier, a finely divided solid carrier, or both, and then, if necessary, shaping the product.

Compositions suitable for oral administration may be presented as discrete units such as capsules, cachettes, tablets, or lozenges, each containing a predetermined amount of the active compound. Other compositions include suspensions in aqueous liquors or non-aqueous liquids such as a syrup, an elixir, or an emulsion.

Other delivery systems can include time-release, delayed release or sustained release delivery systems. Such systems can avoid repeated administrations of the active compounds of the invention, increasing convenience to the subject and the physician. Many types of release delivery systems are available and known to those of ordinary skill in the art. They include polymer based systems such as polylactic and polyglycolic acid, polyanhydrides and polycaprolactone; nonpolymer systems that are lipids including sterols such as cholesterol, cholesterol esters and fatty acids or neutral fats such as mono-, di and triglycerides; hydrogel release systems; silastic systems; peptide based systems; wax coatings, compressed tablets using conventional binders and excipients, partially fused implants and the like. Specific examples include, but are not limited to: (a) erosional systems in which the polysaccharide is contained in a form within a matrix, found in U.S. Pat. No. 4,452,775 (Kent); U.S. Pat. No. 4,667,014 (Nestor et al.); and U.S. Pat. Nos. 4,748,034 and 5,239,660 (Leonard) and (b) diffusional systems in which an active component permeates at a controlled rate through a polymer, found in U.S. Pat. No. 3,832,253 (Higuchi et al.) and U.S. Pat. No. 3,854,480 (Zaffaroni). In addition, a pump-based hardware delivery system can be used, some of which are adapted for implantation.

Use of a long-term sustained release implant may be particularly suitable for prophylactic treatment of ischemia. "Long-term" release, as used herein, means that the implant is constructed and arranged to deliver therapeutic levels of the active ingredient for at least 30 days, and preferably 60 days. Long-term sustained release implants are well known to those of ordinary skill in the art and include some of the release systems described above.

The reduction of ischemic damage by MEK1 inhibitors also enables improvements in organ transplantation perfusion fluids used in the treatment, storage and transport of organs to be transplanted. Thus the invention also provides medical products useful in organ transplantation. In particular, the invention provides organ perfusion fluids containing a MEK1 inhibitor, as well as organs perfused with such perfusion fluids. One of ordinary skill in the art is familiar with standard organ perfusion fluids, including University of Wisconsin solution, Euro-Collins solution, BT01 solution, Ringer's lactate solution and normal saline solution. Other non-MEK1 inhibitor organ perfusion agents which can be added to the foregoing perfusion solutions include calcium entry blockers (e.g. lidoflazine), cytoprotectors (e.g., natriuretic factor, PGI2, trimetazidine), free radical chelating agents and scavengers (e.g., allopurinol, mannitol, glutathione), and substrates for the mitochondrial respiratory chain (e.g., aspartate, glutamate).

EXAMPLES

Methods

Ischemia Model

Adult male SV-129 mice (18–22 g, Taconic Farms, Germantown, N.Y., U.S.A.) were housed under diurnal lighting conditions and allowed food and water ad libitum. Animals were anesthetized with 1.5% halothane and maintained in 1.0% halothane in 70% $N_2O$ and 30% $O_2$ using a Fluotec 3 vaporizer (Colonial Medical, Amherst, N.H., U.S.A.). Ischemia was induced with a 8.0 nylon monofilament coated with silicone resin/hardener mixture (Xantopren and Elastomer Activator, Bayer Dental, Osaka, Japan) as described previously (Huang et al., *Science* 265:1883–1885, 1994).

For treatment with agents or vehicle controls, two microliters of the agent or vehicle (PD98059, SB203580 or dimethyl sulfoxide (DMSO)) were injected i.c.v. (bregma −0.9 mm lateral, −0.mm posterior, −3.1 mm deep) 30 minutes before ischemia using a Hamilton injection syringe.

Immunohistochemistry

Mice were deeply anesthetized with an overdose of sodium pentobarbital (100 mg/kg i.p.) and then transcardially perfused with 0.9% saline solution followed by 4% paraformaldehyde in 0.1M phosphate-buffered saline (PBS) pH 7.4. The brains were quickly removed and stored in the same fresh buffer containing 20% sucrose. Brains were cut into coronal sections of 40 $\mu$m thickness on a freezing microtome. The sections were processed by the free-floating method as described previously (Uemura et al., *Brain Res.* 542:343–347, 1991).

Western Blot Analysis

Ischemic and non-ischemic brains were dounce homogenized in 1 ml potassium phosphate buffer (10 mM $KPO_4$, pH7.05; 1 mM EDTA; 5 mM EGTA; 10 mM $MgCl_2$; 50 mM $\beta$-glycerophosphate; 1 mM sodium vanadate; 1 mM dithiothreitol [DTT]; 0.5% NP-40; 0.1% Brij-35). Lysates were clarified by centrifugation at 14,000 g for 10 minutes. The protein concentration in the supernatant was determined by the Bradford assay (Bio-Rad, Cat. No. 5000-006). To test for phosphorylation of ERK1/2, 40 $\mu$g of total cell lysate was run on a 10% SDS-PAGE gel, transferred onto an Immobilon-P membrane (polyvinylidene fluoride (PVDF) membrane; Millipore Corp., Bedford, Mass., U.S.A.), and a Western blot was performed using phospho-specific p44/42 MAPK antibodies (1:1000) (New England Biolabs, Beverly, Mass., U.S.A.). Proteins were detected using enhance chemiluminescent immunodetection (ECL; Amersham Life Sciences, Piscataway, N.J., U.S.A.). To analyze the protein levels within each lane, the blot was stripped and reprobed, according to Amersham Life Sciences manufacturer's instructions, using C-14 anti-ERK2 antibody (1:1000) (Santa Cruz Biotechnology, Santa Cruz, Calif., U.S.A.).

Analysis of Brain Function

Twenty-two hours after reperfusion, the brains were removed and sliced into five coronal section of 2 mm thickness using a mouse brain matrix (RBM-2000C; Activational System, Mich., U.S.A.). Brain slices were treated with 2% 2,3,5-triphenyltetrazolium chloride (Sigma Chemicals, St. Louis, Mo., U.S.A.), followed by 10% formalin overnight as described previously (Bederson et al., *Stroke* 17:1304–1308, 1986). The infarcted areas, outlined in white, were measured by an image analysis system (MCID ver. 3, Imaging Research, Inc., Ontario, Canada) on the posterior surface of each section and infarction volume was calculated by summing the infarction volume of sequential 2 mm thick sections. For evaluation at 72 hr after reperfusion, the mice were deeply anesthetized with an overdose of pentobarbital and transcardially fixed with 30 ml of 10% formalin in 0.1M PBS. The brains were quickly removed and saturated with 20% sucrose. Fifty micrometer-thick coronal section were cut on a freezing microtome, and every 20th section from the frontal pole was mounted on a glass slide and stained with 0.05% thionin. A coverslip was applied with Paramount (Sigma), and the infarction areas were measured as described above and quantitated by summing the infarction areas of 6 sequential sections. The data were analyzed by standard statistical methods.

Physiology

In randomly selected animals (n=5, 200 $\mu$M PD98059; n=4, 0.4% DMSO), regional cerebral blood flow (rCBF) was measured by Laser-Doppler flowmetry (PF2B, Perimed, Stockholm, Sweden) using a flexible 0.5 mm fiber optic extension to the masterprobe. The tip of the probe was secured 2 mm posterior and 6 mm lateral to the bregma on the ipsilateral hemisphere in animals. Steady-state baseline values were recorded before MCA occlusion, and rCBF during and after occlusion was expressed as percentage of the baseline values. RCBF and arterial blood pressure were monitored using MacLab/8 data acquisition system (AD Instruments, Milford, Mass., U.S.A.) equipped with an ETH 400 transducer amplifier via femoral artery catheterized with a PE-10 polyethylene tubing. Arterial blood samples (50 $\mu$l) were analyzed for pH, oxygen ($pO_2$) and carbon dioxide ($pCO_2$) using a blood gas/pH analyzer (Coming 248, Ciba-Coming Diagnostics, Medford, Mass., U.S.A.). Core temperature was maintained at approximately 36.5° C. with a thermostat (FMC Corp., Brunswick, Ma., U.S.A.) and a heating pad (Watlow, St. Louis, Mo., U.S.A.) during MCA occlusion, and the mice were kept in a warmer (Thermocare, Incline Village, N.J., U.S.A.) for 3 hours after reperfusion.

Example 1

ERK Activation Following Ischemia

Figure 1:
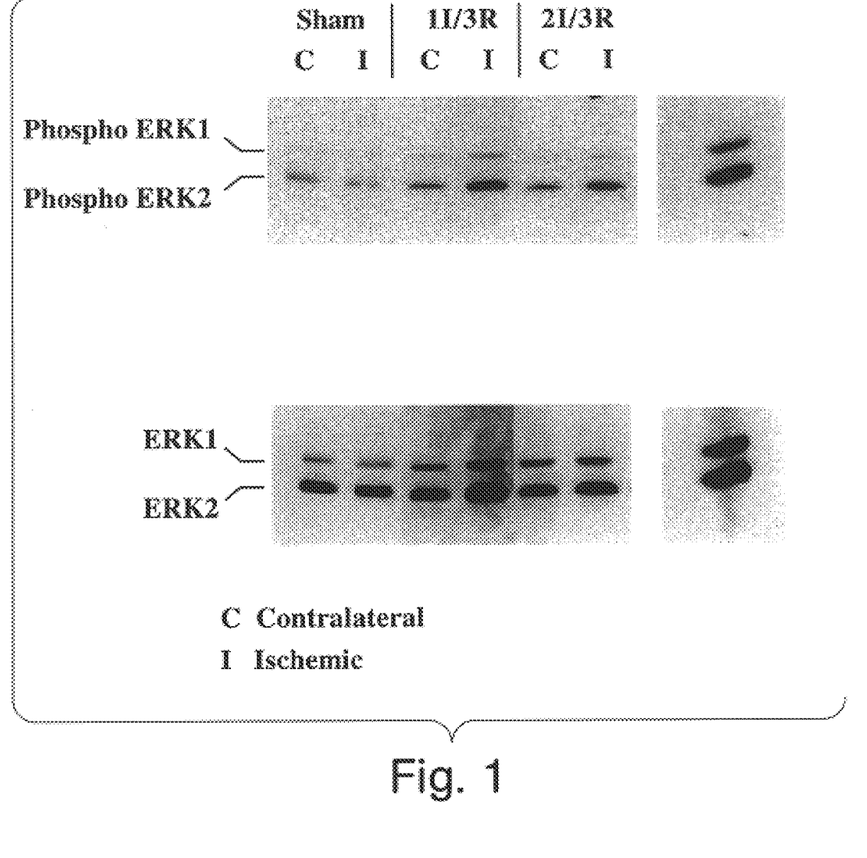
FIG. 1 depicts a Western blot which shows the phosphorylation of ERK1 and ERK2 following cerebral ischemia and reperfusion.

A mouse model of cerebral ischemia was employed to examine the role of the ERK/MAP kinase pathway following ischemia. Cerebral ischemia was induced in SV-129 mice by transient middle cerebral artery (MCA) occlusion for the times given below. Blood flow was restored to assess the effects of reperfusion. Westeren blot analysis was performed on lysates (40 $\mu$l per lane) from the contralateral (C) and ipsilateral/ischemic (I) sides of the brain following 1 hour ischemia (1I) followed by 3 minutes reperfusion (3R) or 2 hour ischemia (2I) followed by 3 minutes reperfusion (3R). ERK2 phosphorylation was increased after 60 or 120 minutes of ischemia followed by 3 minute reperfusion (FIG. 1, upper panel). Amounts of ERK1 /2 protein were detected using ERK-specific antibodies (FIG. 1, lower panel).

Figure 2:
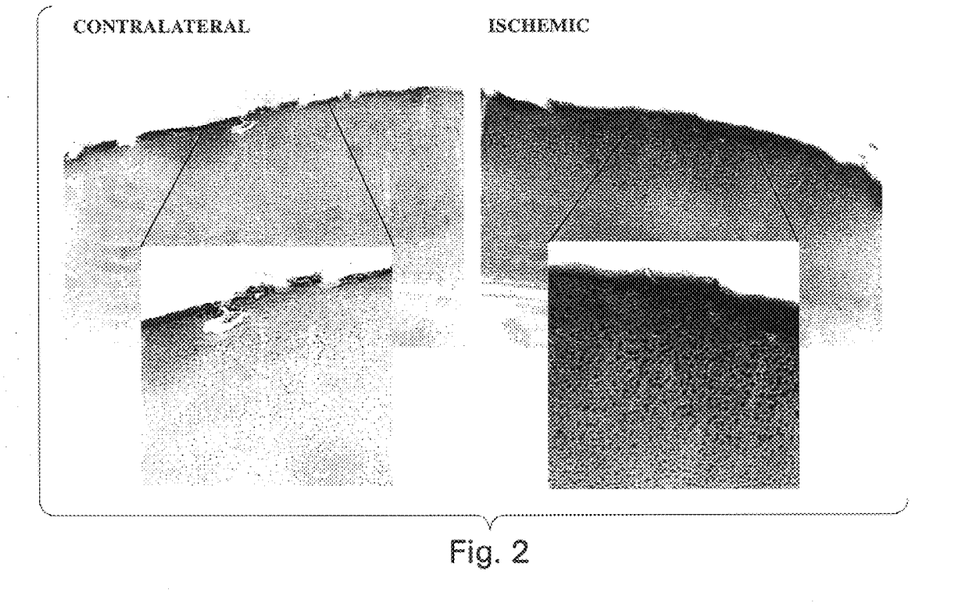
FIG. 2 shows the immunohistochemistry of phosphorylated ERK1/2 in brain slices following ischemia and reperfusion.

Immunohistochemistry of brain sections (40 $\mu$m thickness) was performed using a phospho-specific ERK1/2 antibody (New England Biolabs, Beverly, Mass. ) showed an increase of phosphorylated ERK in the nucleus of cortical cells in the ischemic core, after 60 minutes ischemia and 3 minutes reperfusion (FIG. 2). Contralateral (non-ischemic) and ischemic (ipsilateral) sides of the brain are indicated; magnification was 100×.

Example 2

Inhibition of MEK1 Activity Reduces Ischemia/reperfusion Damage

Figure 3:
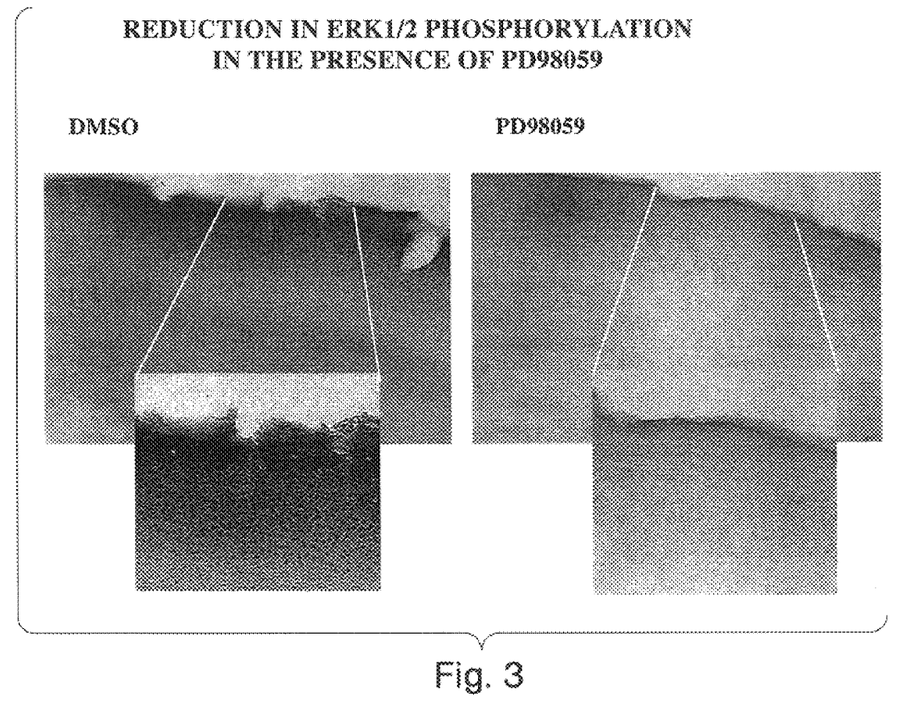
FIG. 3 shows the immunohistochemistry of phosphorylated ERK1/2 in brain slices of animals treated with PD98059 or DMSO control following ischemia and reperfusion.

MEK1 activates the MAP kinases ERK1 and ERK2 by specific phosphorylation. To evaluate the role of MAP kinase activation in neuronal cell damage, the MEK1-specific inhibitor PD98059 (obtained from New England Biolabs) was used to selectively inhibit MEK1 without generally inhibiting other kinases. To inhibit MEK1 in the mouse stroke model, 2 $\mu$l of 200 $\mu$M PD98059 was injected into the cerebral ventricle 30 minutes prior to the induction of focal cerebral ischemia. The control animals were injected likewise with 0.4% DMSO. Following 120 minutes ischemia and 3 minutes reperfusion, immunohistochemistry using the phospho-specific ERK1/2 antibody used in Example 1 demonstrated that phosphorylation of ERK1/2 was reduced in the middle cerebral artery territory in mice pretreated with PD98059 (FIG. 3).

Figure 4A:
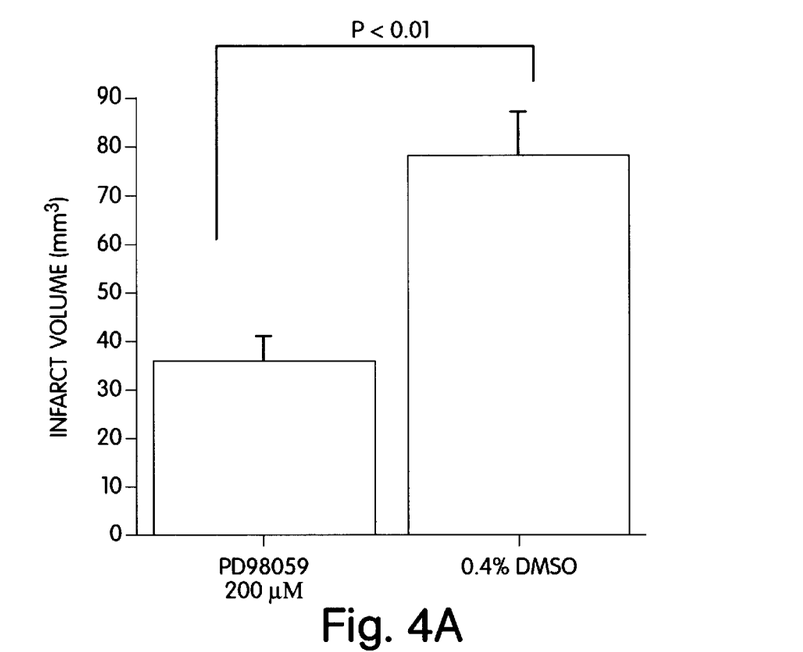
FIGS. 4A, B and C are graphs which show the effect of PD98059 on infarct volume.
Figure 4B:
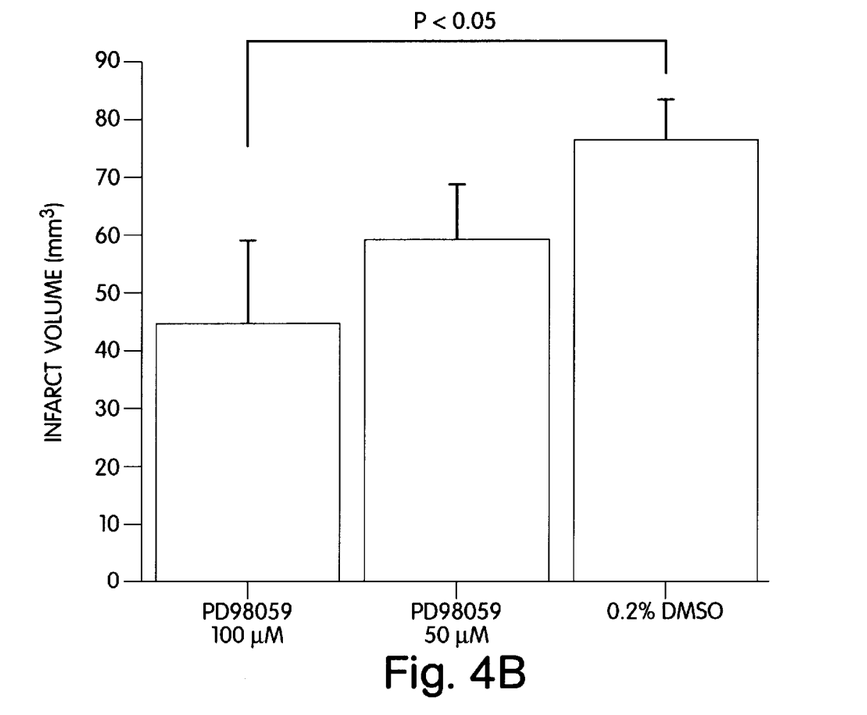
Figure 4C:
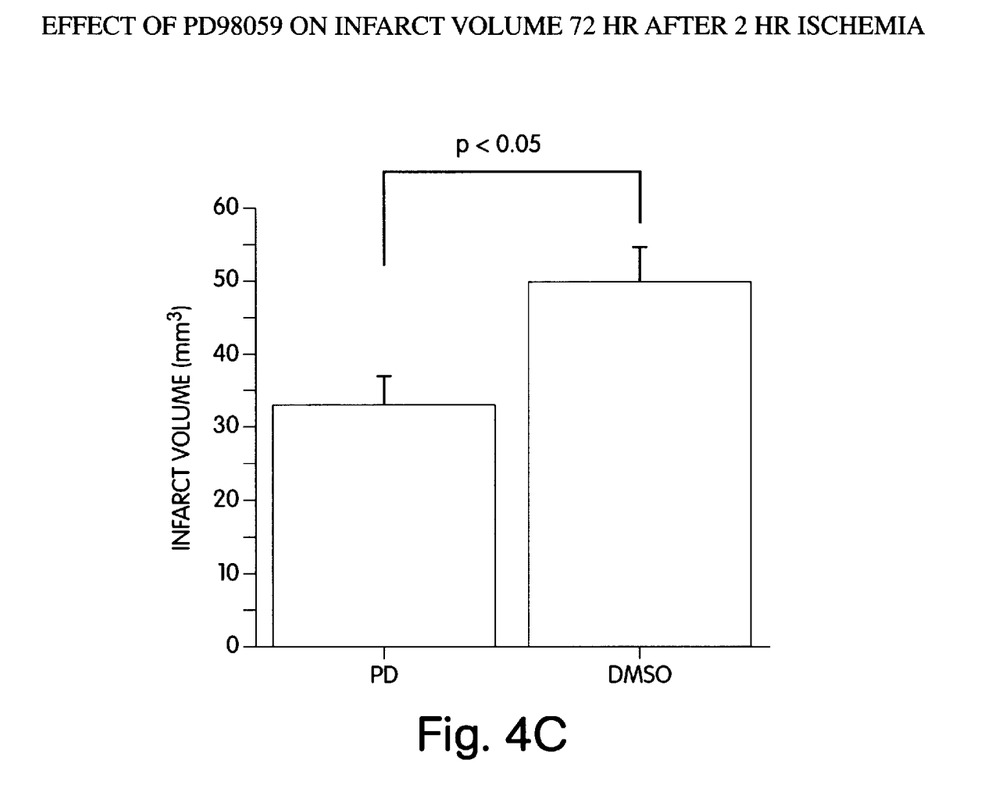

To analyze if PD98059 was a neuroprotective agent, the damage induced by focal cerebral ischemia was assessed using the tetrazolium chloride (TTC) staining method (Bederson et al., *Stroke* 17:1304–1308, 1986). Mice that were pretreated with 200 $\mu$M PD98059 as above showed a 55% (P<0.01) decrease in total damage as determined 22 hours following focal cerebral ischemic insult (FIG. 4A). The neuroprotective ability of the drug is dose-dependent, with a 42% (P<0.05) and a 23% (P<0.05) decrease in total damage observed when mice were pretreated with 100 μM and 50 μM of PD98059, respectively (FIG. 4B). Animals that received 200 μM PD98059 showed a 43% (P<0.05) decrease in total damage three days post-ischemia (FIG. 4C).

Neurological deficits also were significantly attenuated in animal pretreated with PD98059. Neurological deficits caused by ischemia were scored according to Huang et al. (*Science* 265:1883–1885, 1994). Neurological grading three days after 2 hours of MCA occlusion and reperfusion was 0.71±0.29 (s.e.m.) and 2.2±0.3 (P<0.05) in PD98059-treated and vehicle-treated mice, respectively. These data indicate that the inhibition of the MEK1/ERK pathway has long-term neuroprotective significance.

Example 3

Inhibition of MEK1 Activity Does Not Alter Physiological Parameters

To determine if the administration of PD98059 affected the physiology of the treated animals, we measured several physiological parameters.

Regional cerebral blood flow (rCBF) was determined in the presence of absence of 200 μM PD98059 (Table 1). rCBF was determined by Laser-Doppler flowmetry (PF2B, Perimed, Stockholm, Sweden) during 2 hours of middle cerebral artery occlusion and 30 minutes of reperfusion in PD98059 treated and DMSO control treated groups under 1% halothane anesthesia. Data are presented as means±SD. Therefore, the decrease in ERK1/2 phosphorylation seen with PD98059 was not due to higher blood flow.

TABLE 1

| | Regional CBF | |
|---|---|---|
| | PD98059 (n = 5) | DMSO (n = 4) |
| rCBF (during MCA) | 15.9% ± 1.7 | 25.2% ± 5.7 |
| rCBF (after MCA) | 94.9% ± 8.9 | 102.5% ± 6.8 |

Mean arterial blood pressure (MABP) was determined in the presence or absence of 200 μM PD98059 10 minutes before and 1 hour after induction of ischemia, and 30 minutes after reperfusion under 1% halothane anesthesia (Table 2). Data are presented as means±SD. MABP was determined to be unaltered.

TABLE 2

| | Mean arterial blood pressure | |
|---|---|---|
| | PD98059 (n = 5) | DMSO (n = 4) |
| MABP (before) | 86.4 ± 10.9 | 80.7 ± 7.5 |
| MABP (during) | 81.8 ± 4.1 | 82.3 ± 2.1 |
| MABP (after) | 86.0 ± 12.3 | 82.8 ± 13.5 |

Partial oxygen tension ($pO_2$), partial carbon dioxide tension ($pCO_2$), and blood pH were determined in the presence or absence of 200 μM PD98059, 1 hour after the induction of ischemia under 1% halothane anesthesia (Table 3). Data are presented as means±SD. $pO_2$, $pCO_2$, and blood pH did not differ between the two groups.

TABLE 3

| | Physiological variables | |
|---|---|---|
| | PD98059 (n = 5) | DMSO (n = 4) |
| pH | 7.32 ± 0.07 | 7.32 ± 0.06 |
| $pCO_2$ | 49.9 ± 3.5 | 48.8 ± 5.1 |
| $pO_2$ | 139.1 ± 21.6 | 155.3 ± 13.8 |

Body temperature was unaltered up to 22 hours after reperfusion in the PD98059-treated animals when compared to the vehicle-treated controls, with values of 34.6±0.8° C. and 35.9±0.4° C., respectively. In addition, temporal muscle temperature, reflective of head temperature, was unaltered up to three hours after reperfusion in the PD98059-treated animals when compared to the vehicle-treated controls, with values of 35.5±0.1° C. and 35.2±0.3° C. respectively.

Example 4

Specificity of PD98059 Inhibition

The specificity of PD98059 was next evaluated by analyzing whether the stress-induced p38 MAP kinase and SAPK/JNK pathways are mediators of tissue injury in the focal ischemia/reperfusion model. No detectable increase in phosphorylated p38 MAP kinase or phosphorylated c-Jun (a substrate for SAPKs/JNKs) and immunohistochemistry using phospho-specific p38 and phospho-specific c-Jun antibodies (New England Biolabs).

The effect of an inhibitor of these pathways also was determined. SB203580, an inhibitor of p38 MAP kinase (1–2 μM) and SAPKs/JNKs (>10 μM), was administered to animals as described above for PD98059. Two microliters of 100/μM SB203580 or 0.2% DMSO were injected into the lateral ventricle 30 minutes prior to ischemia. SB203580 did not protect the brain from injury relative to vehicle-treated controls as determined by infarct measurement. Thus, the protection observed with PD98059 is due to its specific inhibition of the MEK1/ERK pathway.

Those skilled in the art will recognize, or be able to ascertain using no more than routine experimentation, many equivalents to the specific embodiments of the invention described herein. Such equivalents are intended to be encompassed by the following claims.

All references disclosed herein are incorporated by reference.

What is claimed is:

1. A method for treating a subject having a condition characterized by ischemia comprising administering to a subject in need of such treatment a MEK1 inhibitor in an amount effective to reduce MEK1 activity, wherein the subject is free of symptoms otherwise calling for treatment with the MEK1 inhibitor.

2. The method of claim 1, wherein the symptoms otherwise calling for treatment with the MEK1 inhibitor are the symptoms of a proliferative disease.

3. The method of claim 1, wherein the MEK1 inhibitor is a tricyclic flavone.

4. The method of claim 3, wherein the MEK1 inhibitor is 2-(2-amino-3-methoxyphenyl)-4-oxo-4H-[1]benzopyran.

5. The method of claims 1–4, wherein the MEK1 inhibitor is administered to a subject who has had an ischemic stroke.

6. The method of claims 1–4, wherein the MEK1 inhibitor is administered prophylactically to a subject at risk of having an ischemic stroke.

7. A pharmaceutical composition comprising a MEK1 inhibitor, and a non-MEK1 inhibitor anti-stroke agent, together in an amount effective for treating an ischemic condition.

8. A kit comprising a package housing a first container containing a MEK1 inhibitor, and instructions for using the MEK1 inhibitor in the treatment of an ischemic condition.

9. The kit of claim 8, further comprising a second container containing a non-MEK1 inhibitor anti-stroke agent.

10. A medical product comprising an isolated organ in a perfusion fluid containing a MEK1 inhibitor.

11. A medical product comprising an organ perfusion fluid containing a MEK1 inhibitor.

* * * * *